United States Patent
Reinhardt et al.

(10) Patent No.: US 6,311,334 B1
(45) Date of Patent: Nov. 6, 2001

(54) COMPRESSION HOSE FOR THE TREATMENT OF LEG CONDITIONS

(75) Inventors: Holger Reinhardt, Kempen; Hans B. Bauerfeind, Zeulenroda, both of (DE)

(73) Assignee: Bauerfeind Orthopadie GmbH & Co. KG (DE)

( * ) Notice: Subject to any disclaimer, the term of this patent is extended or adjusted under 35 U.S.C. 154(b) by 0 days.

(21) Appl. No.: 09/668,137

(22) Filed: Sep. 25, 2000

(30) Foreign Application Priority Data

Sep. 17, 1999 (DE) .............................................. 299 17 030
Sep. 25, 1999 (DE) .............................................. 199 46 019

(51) Int. Cl.⁷ .............................. A41B 11/02; A43B 17/00
(52) U.S. Cl. .................................................................. 2/239
(58) Field of Search .............................. 2/239, 240, 241, 2/242, 22; 66/178; 442/16, 182, 183, 184, 185; 428/105

(56) References Cited

U.S. PATENT DOCUMENTS

| | | | |
|---|---|---|---|
| 3,616,130 | * 10/1971 | Rogosch | 161/57 |
| 4,060,075 | * 11/1977 | Blomer et al. | 128/90 |
| 4,106,313 | * 8/1978 | Boe | 66/202 |
| 4,172,456 | * 10/1979 | Zens | 128/165 |
| 4,565,745 | * 1/1986 | Kaminskas | 428/596 |
| 4,905,692 | * 3/1990 | More | 606/151 |
| 5,048,513 | * 9/1991 | Reinhardt | 128/156 |
| 5,181,906 | * 1/1993 | Bauerfeind | 602/63 |
| 5,497,513 | * 3/1996 | Arabeyre et al. | 2/240 |
| 5,972,502 | * 10/1999 | Jessee et al. | 428/370 |
| 6,119,491 | * 9/2000 | Pinelli | 66/177 |
| 6,123,681 | * 9/2000 | Brown, III | 602/75 |
| 6,173,452 | * 1/2001 | Kelly et al. | 2/240 |
| 6,204,207 | * 3/2001 | Cederblad et al. | 442/5 |

FOREIGN PATENT DOCUMENTS 92 01 000.8  3/1992 (DE) .
44 12 040  11/1994 (DE) .

* cited by examiner

Primary Examiner—John J. Calvert
Assistant Examiner—Alissa L. Hoey
(74) Attorney, Agent, or Firm—Banner & Witcoff, Ltd.

(57) ABSTRACT

The invention relates to a compression hose made of elastic textile base material for the treatment of leg conditions, a rhombic lattice being integrated into the base material, with diagonals of the rhombuses lying in the longitudinal direction of the hose, and with intersecting strips which extend hexically and continuously obliquely relative to the longitudinal direction of the hose and form the rhombic lattice, the elasticity of these strips being less than the base material enclosed by the strips, and the length of the hose in each case defined by longitudinal stretching of the hose determining its compression pressure.

8 Claims, 3 Drawing Sheets

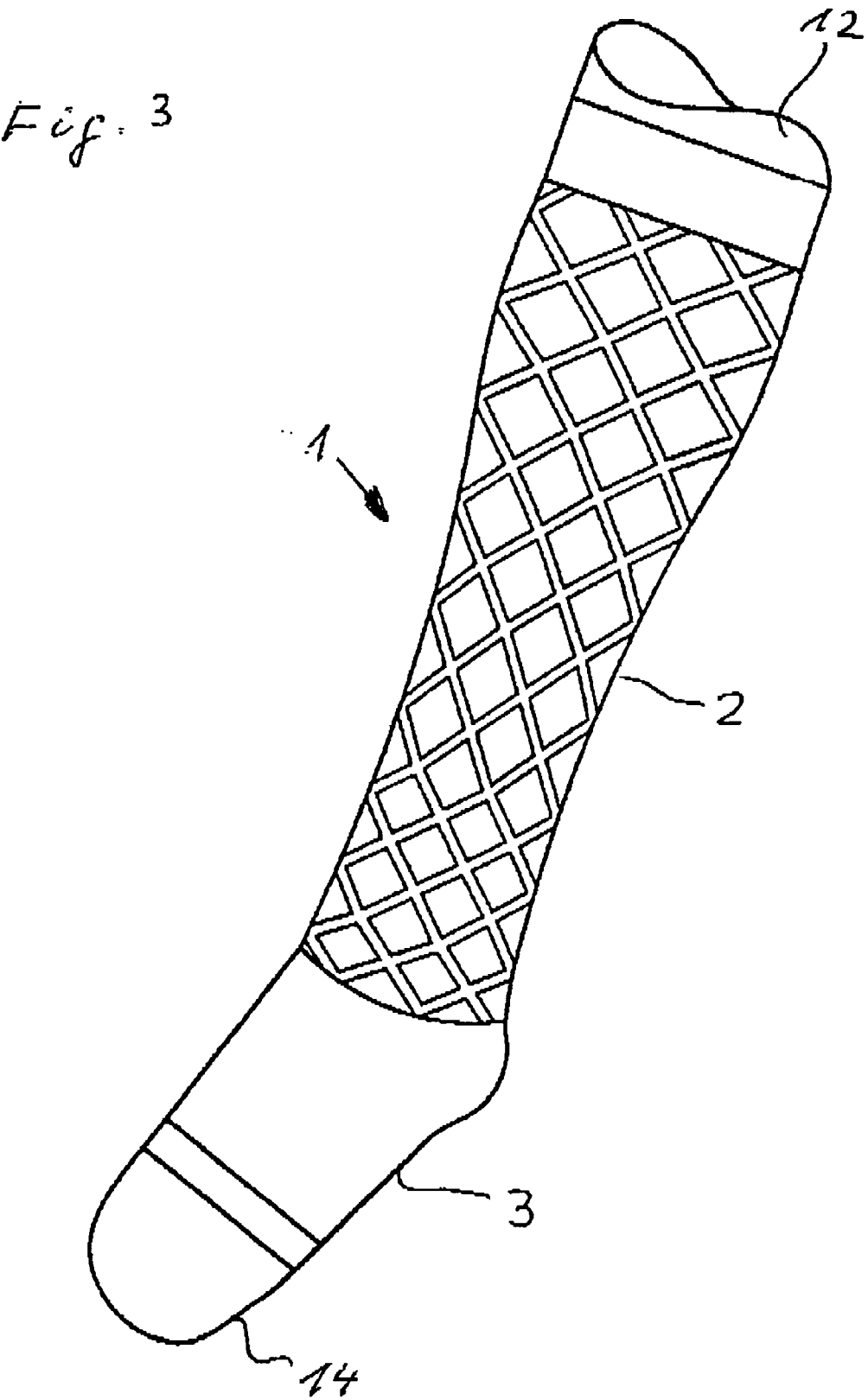

COMPRESSION HOSE FOR THE TREATMENT OF LEG CONDITIONS

Figure 1:
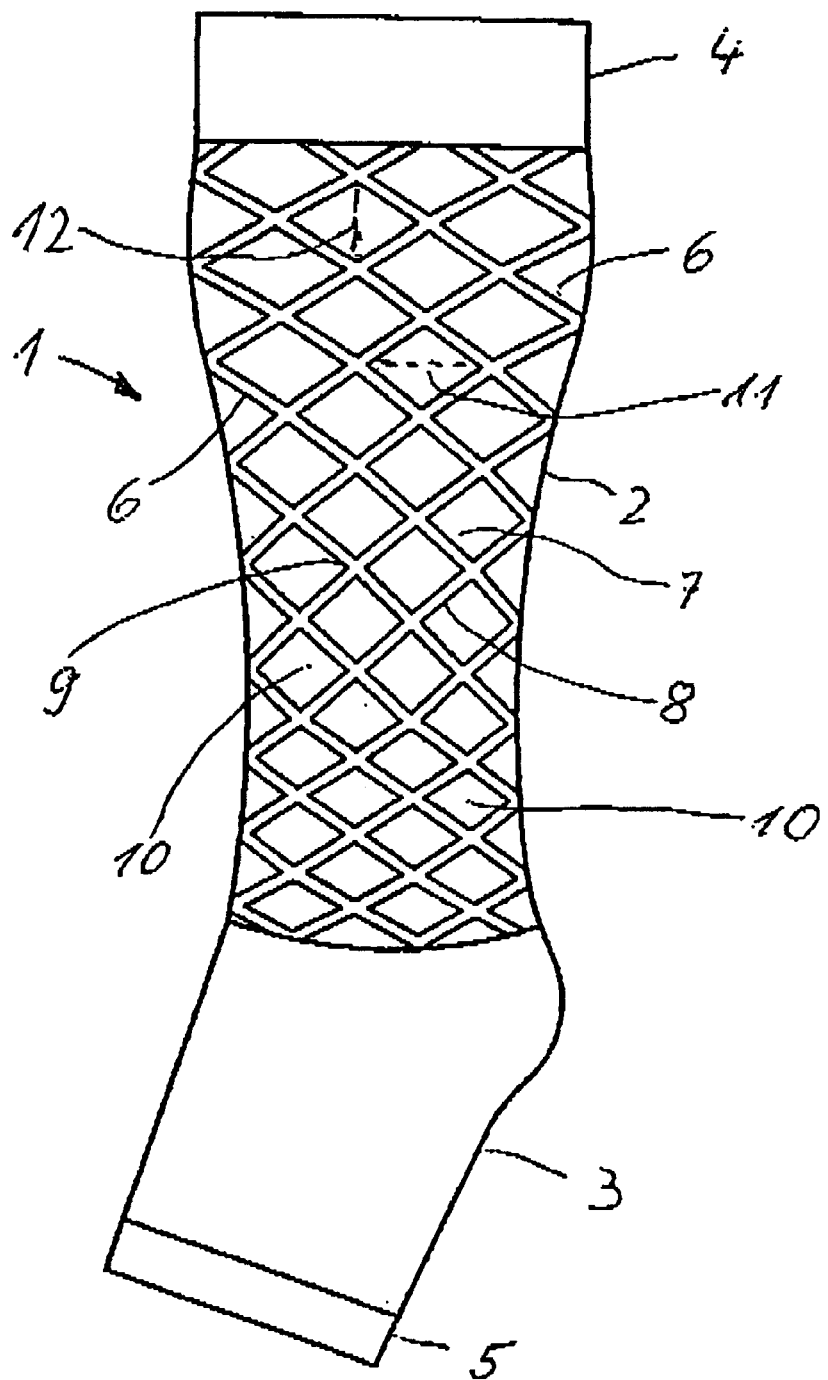

The invention relates to a compression hose made of elastic textile base material for the treatment of leg conditions.

Such compression hoses are mostly use together with a foot part, thereby constituting a compression stocking. In the case of such compression stockings, in order to generate a particularly high pressure on the leg which is to be treated, several compression stockings have already been applied one over the other in accordance with DB GBM 29001000.8, thereby affording a corresponding increase in pressure. When treating leg conditions by means of compression stockings, it is necessary to take into account the measurements of the patient's leg which is to be treated and the particular compression pressure which is required in each case. This normally involves the use of compression hoses with an attached foot part, which combination then forms the complete compression stocking in which, nevertheless, the desired therapeutic effect derives from its compression hose. To satisfy these requirements, compression stockings are produced in different sizes and from different materials, it being possible to achieve a particularly desired compression pressure in each case on the basis of the different materials. For this purpose, a considerable number of differently designed compression stockings are needed, which entails correspondingly high production outlay, since a correspondingly large number of different compression stockings normally have to be made available to take account of the various requirements.

The object of the invention is to design a compression hose which, essentially in one size, can be adapted to different leg sizes and additionally allows a desired individual compression pressure to be set. In connection with the compression hose mentioned in the introduction, this problem is solved by the fact that a rhombic lattice is integrated into the base material, with diagonals of the rhombuses lying in the longitudinal direction of the hose, and with intersecting strips which extend helically and continuously obliquely relative to the longitudinal direction of the hose and form the rhombic lattice, the elasticity of these strips being less than the base material enclosed by the strips, and the length of the hose in each case defined by longitudinal stretching of the hose determining its compression pressure.

The rhombic lattice integrated into the elastic textile base material acts along the entire length of the compression hose such that a compression hose set to a short length is widened to a relatively large diameter, its compression pressure being determined by this diameter. If, by contrast, the compression hose is stretched to a greater length, it has a correspondingly smaller diameter, so that the compression hose can be used on a relatively thin leg. If a particularly high compression pressure is then needed, this can be achieved by expanding the hose. Here, the function of the rhombic lattice plays a decisive role since, upon shortening of its diagonals lying in the longitudinal direction of the hose (longitudinal diagonals), the rhombic lattice widens correspondingly, and does so on account of the associated lengthening of the transverse diagonals which extend in the circumferential direction of the compression hose. If, by contrast, the compression hose is stretched in its longitudinal direction, the abovementioned transverse diagonals of the individual rhombuses shorten, with the compression hose contracting and exerting a correspondingly increased pressure on the leg which is to be treated. The said rhombic lattice thus makes it possible to take account of the dimensions of the leg to be treated by corresponding adaptation of the diameter of the compression hose, and also to set selectively the compression pressure of the compression hose in each case. Thus, the compression hose according to the invention covers a wide range of applications, including both thin and thicker legs and permitting a considerable variation in the required compression pressure. Thus, a single size of the compression hose according to the invention can be used to a large extent to satisfy conditions which vary quite considerably from patient to patient, and this considerably simplifies its production and reduces its production costs.

The use of a criss-cross plaiting of bands for an orthopaedic stocking for the thigh extension is known per se, namely from DE-OS 4,412,040. That document concerns pulling a hose, designated as a stocking, over the thigh the hose projecting by a defined length past the end of the leg (possibly a leg stump) and here being exposed to a load, whereupon the hose in the area of the thigh contracts and thus bears on the thigh with such firmness that the hose cannot slip off from the thigh, This is intended to facilitate application of tensile forces to the thigh, by which means it is then possible to act on the thigh and thus on the hip joint via the tensile forces applied to the thigh. Thus, no adjustable compression pressure is conceived of in this case.

The rhombic lattice permitting the above-mentioned adaptability of the compression hose can be knitted into the base material. Compression stockings are normally made of a knitted textile base material, so that the hose part of such compression stockings is created by a patterning of the base material known for knitting. A preferred patterning entails preventing mesh formation in the area of the intersecting strips, so that these positions have a shortened thread run in which is the elasticity afforded by a mesh formation is absent, which simply means that at the positions concerned the elasticity of the strip is reduced. The intersecting strips of lesser elasticity thus form the rhombic lattice in which, at the intersections of the strips, the knitting process used has the effect that, in the area of its strips, the rhombic lattice causes the transverse diagonals of the individual rhombuses to contract to a greater or lesser extent depending on the longitudinal stretching of the hose, which then permits the adaptation to the particular leg size and the setting of the required compression pressure.

A further possibility for integration of the rhombic lattice is for the latter to be bonded or welded onto the base material. In this case, the rhombic lattice can consist of an elastic foil material from which the rhombic lattice is punched out or cut out, so that a rhombic lattice consisting of intersecting strips is provided, which is then placed on the compression hose, in order then to be bonded on or welded on by heating. The foil material used for this purpose is elastic, but its elasticity is less than that of the base material.

However, it is possible to influence the base material itself to form the strips, to be specific in such a way that a local welding or bonding of the base material takes place in the area of the strips, and this is made possible by the base material being acted upon by radiation while covered by a corresponding mask, from which only the areas of the strips are left free, so that heating takes place in these areas, which leads to welding or bonding of the base material in the area of the strips.

A further possibility for forming the rhombic lattice is to apply a liquefied plastic to the base material, following the intersecting strips of the rhombic lattice, whereupon the liquefied plastic is hardened, with the result that the rhombic lattice has a correspondingly lower elasticity in the area of the hardened plastic.

It should be noted that the above-described compression hose can of course also be provided with a foot part, thus resulting overall in a compression stocking.

Figure 2:
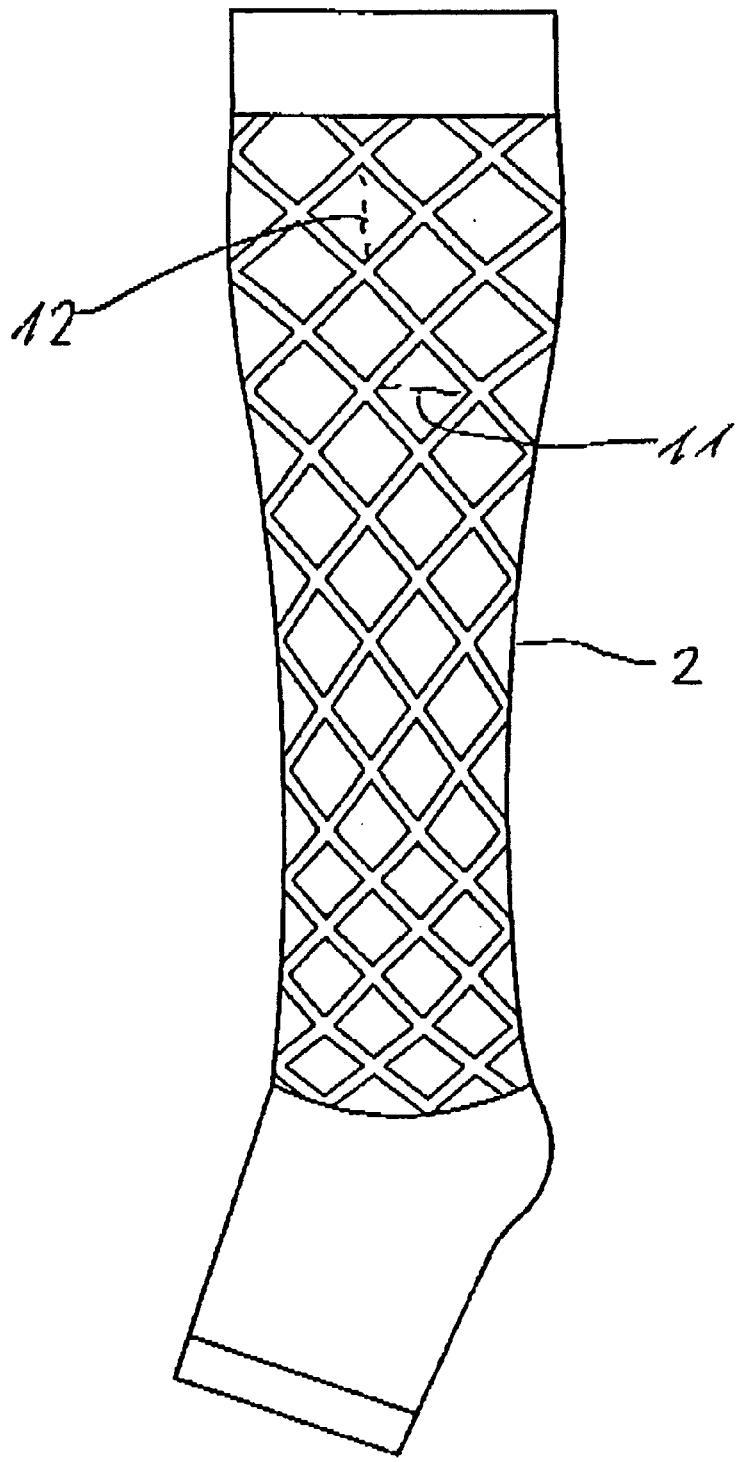

An illustrative embodiment of the invention is represented in the figures, in which:

FIG. 1 shows a compression stocking with a compression hose in which the rhombic lattice is formed, in the unstressed state without longitudinal stretching, FIG. 2 shows the same compression stocking with longitudinal stretching, FIG. 3 shows the compresson hose applied to a lower leg and with a foot part, thus overall forming a compression stocking stretched according to FIG. 2.

FIG. 1 shows the compression stocking 1 consisting of the compression hose 2 and of the foot part 3, the compression hose 2 being delimited at the top by the end edge 4, and the foot part 3 ending in the foot closure 5. Compression hose 2 and foot part 3 are securely connected to each other.

The compression hose 2 consists of an elastic textile base material, in particular a compression knit, into which the rhombic lattice 6 according to this illustrative embodiment is knitted. The rhombic lattice 6 is in this case formed by the strips 7 and 8 which each extend helically about the compression hose 2, according to a right-hand thread and a left-hand thread, respectively. The intersections 9 of the strips 7 and 8 result in individual rhombuses 10, which are thus each enclosed by four strips 7 or 8. Within these rhombuses 10, the base material enclosed by the strips 7 and 8 forms the relevant part of the compression hose. The strips 7 and 8 are so configured that their elasticity is less than the base material enclosed by the strips 7 and 8 in the area of each rhombus. This results in the rhombic lattice 6 which can be seen in FIG. 1, which acts on the compression hose in the above-described manner so that upon longitudinal stretching of the compression hose 2, the transverse diagonals 11 contract, while the longitudinal diagonals 12 are lengthened as a result of the longitudinal stretching.

It should also be noted that the view of the rhombic lattice 6 shown in FIG. 1 naturally extends about the entire compression hose 2, thus resulting in a complete tubing made up of the rhombic lattice 6 in the form of the compression hose 2. The strips can in this case also be thread-like.

In FIG. 2, the compression hose 2 according to FIG. 1 is shown in a longitudinally stretched, longitudinally expanded position in which the transverse diagonals 11 have been correspondingly shortened and the longitudinal diagonals 12 are lengthened. As a result of this longitudinal stretching of the compression hose 2, its length is lengthened in particular for adaptation to the length of leg of a correspondingly tall patient.

This type of shortening or lengthening of the compression hose by longitudinal stretching or longitudinal expansion, with the associated narrowing or widening of the diameter of the compression hose, can of course go beyond the dimensions indicated in FIGS. 1 and 2 in order in this way to adapt the compression hose to different leg sizes and to different compression pressure requirements.

In FIG. 3, the compression hose 2 represented in FIG. 2 is shown as a compression stocking 1 arranged on a lower leg 13. The toe area 14 shown in simplified manner projects from the foot part 3. A compression stocking 1 fitted with the compression hose 2 according to the invention, and adapted to the individual conditions, can in this way be readily placed on any lower leg, the stretch properties of the rhombic lattice permitting wide-ranging adaptation of the compression stocking to very different lower leg sizes.

What is claimed is:

1. Compression hose (2) made of elastic textile base material for the treatment of leg conditions, characterized in that a rhombic lattice (6) is integrated into the base material, with diagonals (12) of the rhombuses (10) lying in the longitudinal direction of the hose, and with intersecting strips (7, 8) which extend helically and continuously obliquely relative to the longitudinal direction of the hose and form the rhombic lattice (6), the elasticity of these strips being less than the base material enclosed by the strips (7, 8), and the length of the hose (2) in each case defined by longitudinal stretching of the hose (2) determining its compression pressure.

2. Compression hose according to claim 1, characterized in that the rhombic lattice (6) is knitted into the base material.

3. Compression hose according to claim 1, characterized in that the rhombic lattice (6) is adhesively bonded on.

4. Compression hose according to claim 1, characterized in that the rhombic lattice (6) is welded on.

5. Compression hose according to claim 1, characterized in that the rhombic lattice (6) consists of an elastic foil material.

6. Compression hose according to claim 1, characterized in that the rhombic lattice (6) is formed by local welding or bonding of the base material in the area of the strips.

7. Compression hose according to claim 1, characterized in that the rhombic lattice (6) is applied as liquefied plastic to the base material and is hardened after application.

8. Compression hose according to claim 1, characterized in that it ends in a foot part (3).

* * * * *